US00PP11636P

United States Patent [19]

Van der Salm et al.

[11] Patent Number: Plant 11,636

[45] Date of Patent: Nov. 14, 2000

[54] LILIUM PLANT NAMED 'GEORGETTE'

[75] Inventors: Catherine Joy Van der Salm, Woodland; Judith Louise Freeman, Vancouver, both of Wash.

[73] Assignee: Van der Salm Bulbfarm, Inc., Woodland, Wash.

[21] Appl. No.: 09/217,375

[22] Filed: Dec. 21, 1998

[51] Int. Cl.[7] ..... A01H 5/00

[52] U.S. Cl. ..... Plt./315

[58] Field of Search ..... Plt./315, 313

*Primary Examiner*—Howard J. Locker
*Assistant Examiner*—Michelle Kizilkaya

[57] ABSTRACT

A new variety of hybrid lily plant bearing large outfacing to upfacing flowers of excellent form and long persistence, both on the plant and as cut-flowers. The flowers of the new plant are particularly characterized by their large size and substance, their starry flower form, their lightly ruffled outer tepals, their outfacing to upfacing orientation, their ascending pedicels, their yellow coloration with a deeper flush of rich yellow along the basal midribs, and their inconspicuously colored papillae. This combination is completely new in the Oriental and Oriental/Aurelian hybrid lilies. The bulbs may be precooled and forced for cut-flower production under a wide range of light and temperature conditions. The clone is vigorous and is a good grower and propagator.

1 Drawing Sheet

BACKGROUND OF THE INVENTION

Our new variety of lily plant originated as an embryo-cultured seedling which first flowered in Woodland, Wash., in 1995. The breeding efforts had as their objective the production of large-flowered Oriental and Oriental/Aurelian hybrids in shades of yellow, gold, and peach, suited to forcing into flower out of season, heretofore unknown in the lily breeding art.

Catherine J. Van der Salm achieved the desired objective by pollinating a yellow-banded white Oriental/Aurelian hybrid with a soft gold flowered Oriental/Aurelian hybrid. The unnamed Oriental/Aurelian seedling which was the mother plant of 'Georgette' was a hybrid between the Oriental Lilium 'White Mountain' and a second-generation Oriental/Aurelian hybrid. This mother plant was produced by embryo culturing by Judith L. Freeman. The pollen parent was a complex second-generation Oriental/Aurelian hybrid with large, wide tepalled golden yellow flowers, produced by embryo culturing by Judith L. Freeman from a cross between an outfacing yellow complex Oriental/Aurelian hybrid and a pendant buff to gold complex Oriental/Aurelian hybrid. Judith L. Freeman produced one of the original paternal grandparents by embryo-culturing as well, from material unique to her own breeding lines and not available in the trade.

The flowers of our new lily are characterized by an outfacing to upfacing orientation, large size, starry form, ascending pedicels, and particularly by their yellow coloration with a deeper flush of rich yellow along the basal midribs and with inconspicuously colored papillae and lightly ruffled outer tepals. This combination is completely new in the Oriental and Oriental/Aurelian hybrid lilies. In addition, the clone possesses to a high degree desirable characteristics of hybrid vigor. The clone is a good grower and propagator, as observed at Woodland, Wash.

Our new variety of lily plant has been asexually reproduced by us and under our direction at Woodland, Wash. Successive generations produced by natural propagation from bulblets, by bulb scale propagation, and by tissue culturing from bulb scale explants have demonstrated that the novel and distinctive characteristics of our new variety are fixed and hold true under asexual propagation from generation to generation.

DESCRIPTION OF THE DRAWING

Our new variety of lily plant is illustrated in the accompanying photographic drawing, which shows the open bloom in full color and illustrates the starry flower form and upfacing to outfacing orientation, the tepal arrangement, the ascending pedicels, the lightly ruffled outer tepals, and in particular the novel and distinctive yellow coloration with a deeper flush of true yellow along the basal midribs. This combination is completely new in the Oriental and Oriental/Aurelian hybrid lilies.

DESCRIPTION OF THE NEW VARIETY

The following is a detailed description of our new hybrid lily, with nomenclature according to the International Lily Register (Royal Horticultural Society of London, Second Edition, 1969), and with color designations according to the Colour Chart of The Royal Horticultural Society, published by the Society in 1966.

The Plant

Origin: Seedling.

Seed parent: Selected unnamed complex Oriental/Aurelian hybrid seedling, produced by embryo culturing.

Pollen parent: Selected unnamed complex Oriental/Aurelian hybrid seedling, produced by embryo culturing.

Commercial classification: Hybrid Lilium clone.

Horticultural classification: Division VII-B, bowl-shaped Oriental hybrid lily, or Division VIII ("to contain all hybrids not provided for in any other division"), according to the Horticultural Classification of Lilies, Royal Horticultural Society of London. 'Georgette' genetically links Division VII with Division VI; in plant and flower form and in growing characteristics it is distinctly Oriental (Division VII), but its unique flower coloration shows its Aurelian heritage (Division VI) as well.

Form: Single stem, erect and stately.

Height: 85 to 125 cm from bulbs 14 to 18 cm in circumference, provided their light levels are adequate; low light levels may cause "stretching."

Growth: Vigorous and upright.

Foliage quantity: Abundant.

Size of leaf: Broad, 4 to 7 cm wide×11 to 20 cm long.

Shape of leaf: Lanceolate (pointed).

Texture of leaf: Leathery and glossy.

Color of leaf: Mature upper leaf surfaces are R.H.S. CC yellow-green 139 A, juvenile upper leaf surfaces are R.H.S. CC yellow-green 137 B and both mature and juvenile lower leaf surfaces are R.H.S. CC yellow-green 137 C).

Bulb size: Any size, ranging to 25 cm circumference commercially

Bulb color: White to soft yellow, with flushes of deep pink or deeper yellow after exposure to light.

The Bud

Form: Obtuse, ovoid, and long.

Size: 11 to 16 cm long and 10 to 14 cm in circumference just prior to opening.

Opening: Bud opens slowly, in response to morning light; this takes about one hour.

Color: Soft yellow (R.H.S. CC yellow-orange 18 B to 18 C to 16 D) with soft green midribs, often overlaid with soft pink plum, just prior to opening.

Peduncle: Averages 2 to 6 cm, but it may elongate if light levels are too low or if bulbs have been improperly stored prior to forcing. Color is dark green with plum overlay.

The Flower

Blooming habit: Annually in midseason; flowers once and profusely.

Size: Flowers are large-sized, averaging 18 to 26 cm in diameter, reflexing at the tips on the second day to 14 to 22 cm in diameter. The outer tepals are 4 to 5 cm wide; the inner tepals are 5 to 6 cm wide, narrowing rather than overlapping at their bases.

Borne: In a single racemic inflorescence producing 3 to 6 flowers from a bulb 14 to 16 cm in circumference.

Shape: Forms a broad bowl shape by the second day after opening, with the "bowl" 4 to 6 cm deep. Bowl may open wider to approach a "flat face" form as flower ages.

Tepalage: Typical of genus Lilium, with 6 imbricated tepals.

Tepal color: The underlying color if R.H.S. CC yellow-orange 16 C to 16 D, shading to yellow 11 C to 11 D at the tepal margins; a deeper slightly golden yellow (R.H.S. CC yellow-orange 16 A to 16 B) overlays this yellow in a wash 1–3 cm wide on each tepal, deepest at the midrib and extending from the base to the point of tepal recurve. Cool temperatures and bright light levels accentuate the gold tones; low light levels and extreme heat make the color slightly lighter and slightly more yellow to greenish-yellow.

Tepal spotting: The basal half of each inner tepal is lightly spotted with small, inconspicuous papillae which are only slightly deeper in color (R.H.S. CC 16 A to 16 B) than the tepal centers. The papillae are only slightly raised, and they are elongate parallel to the veins of the tepals. The outer tepals have only a few papillae, which are small and inconspicuous.

Nectaries: Apple green nectaries are bordered with a 1–2 mm yellow margin.

Tepal longevity: Tepals stay on stems about three weeks.

Pedicel length: Average 8 to 15 cm long

Pedicel color: Dark green

Pedicel form: Sturdy, flexible, and ascending.

Color changes: Flowers may become slightly lighter and more yellow as they age. Low light levels and extreme heat may cause color to become lighter. Cool temperatures and bright light levels will intensify the color.

Appearance: Flower is slightly shiny.

Disease resistance: The flower and plant are resistant to disease; in particular, they are somewhat resistant to Fusarium bulb rot and very resistant to Botrytis blight.

Fragrance: Slight sweet fragrance.

Lasting quality: The flower is long lasting, both on the plant and as a cut-flower.

The Reproductive Organs

Stamens: Arrangement typical of genus Lilium. Six stamens with soft yellow (R.H.S. CC yellow 11 B to 11 C) to soft green filaments 8 to 10 cm long.

Pollen and anthers (dehisced): R.H.S. CC greyed orange 169 A to 169 B.

Pistil: One in number, 10 to 12 cm long; style is soft green.

Stigma: Light greyed purple (R.H.S. 186C to 186D) to light green; medium in size.

Characteristics of ovary: Characteristic of genus Lilium.

The Fruit

Fertility: The fruit bears only a few embryos and only rarely fertile seed.

Shape: Ovoid.

Color at maturity: Soft brown, overlaid with soft plum.

Our new variety of Oriental hybrid lily most nearly resembles Lilium 'Golden Stargazer' (U.S. Plant Pat. No. 9,794) in plant habit, foliar characteristics, and inflorescence. Its flowers are more yellow and less golden; and its flower form is distinctly starrier, with narrower inner tepals which do not overlap at the base. Unlike 'Golden Stargazer', its outer tepals are distinctly ruffled along their margins; and its inconspicuous papillae are only slightly deeper in color than the tepal centers, never showing shades of peach or deep gold.

We claim:

1. A new and distinctive variety of Oriental hybrid lily plant substantially as herein shown and described, characterized by its high resistance to disease; its vigorous growth and rapid natural propagation; the excellence of its flower form, size, and substance; its versatility both as a garden plant and as a cut-flower producer from pre-cooled bulbs forced under glass out of season; and in particular by its outfacing to upfacing buds, its ascending pedicels, and by its unique yellow coloration, with deeper yellow basal midrib, inconspicuous papillae and lightly ruffled outer tepals, a combination unique among Oriental and Oriental/Aurelian hybrid lilies suited to forcing and to mass commercial cultivation.

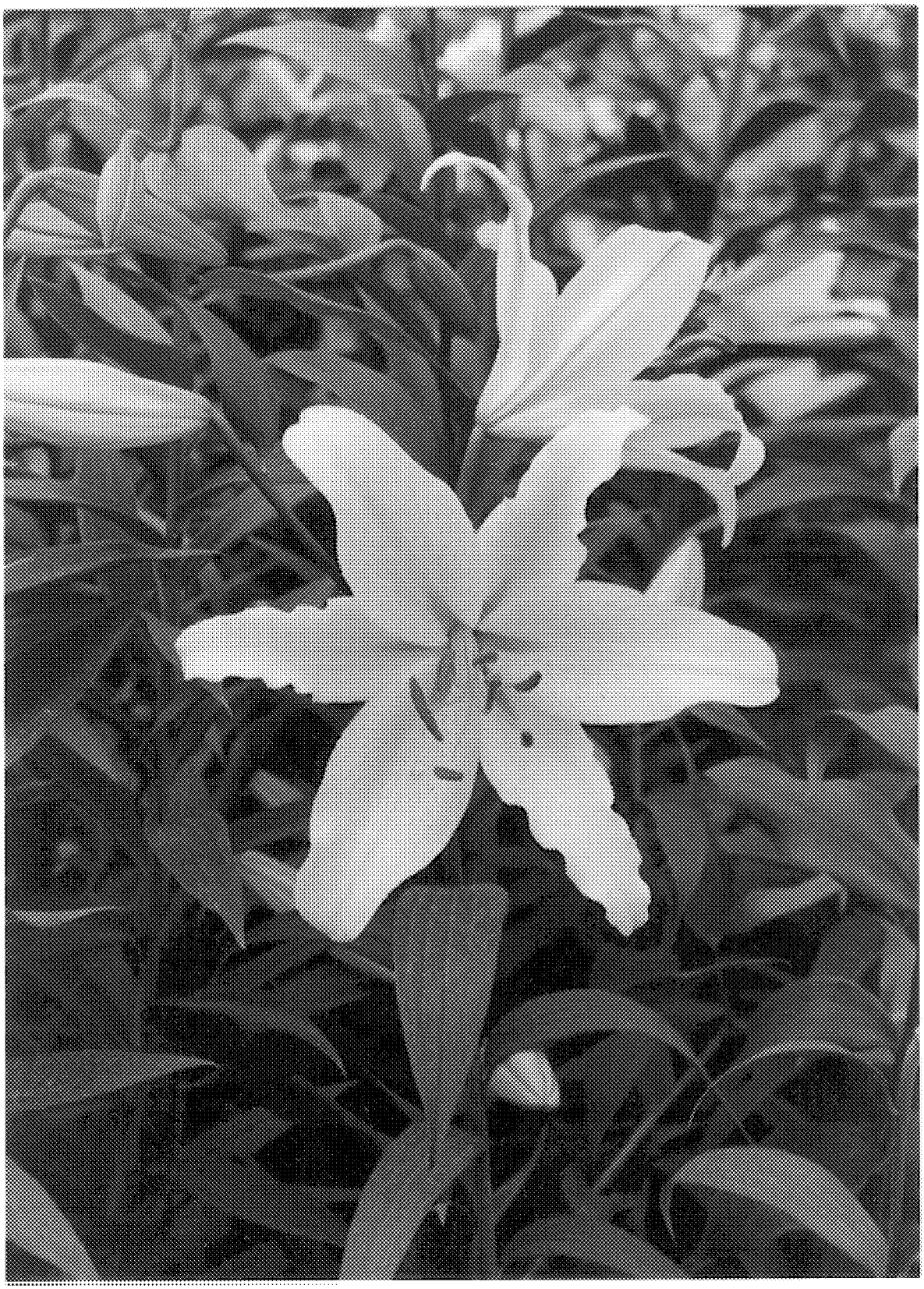

* * * * *